United States Patent [19]

Violanto et al.

[11] Patent Number: 4,826,689
[45] Date of Patent: May 2, 1989

[54] METHOD FOR MAKING UNIFORMLY SIZED PARTICLES FROM WATER-INSOLUBLE ORGANIC COMPOUNDS

[75] Inventors: Michael R. Violanto, Harry W. Fischer, both of Rochester, N.Y.

[73] Assignee: University of Rochester, Rochester, N.Y.

[21] Appl. No.: 735,459

[22] Filed: May 17, 1985

[51] Int. Cl.⁴ ............................................. A61J 3/02
[52] U.S. Cl. ................................ 424/489; 210/709; 210/729; 210/639; 264/9; 424/492; 514/951; 514/965
[58] Field of Search ............... 210/634, 702, 710, 729, 210/737, 738, 768, 772, 773, 709, 746, 96.1, 639; 702/401, 402; 264/9; 424/14, 19, 489, 490, 492, 497; 514/951, 965

[56] References Cited

U.S. PATENT DOCUMENTS

| | | | |
|---|---|---|---|
| 2,340,672 | 2/1944 | Lister | 210/634 |
| 2,776,241 | 1/1957 | Priewe et al. | 167/95 |
| 2,919,181 | 12/1959 | Reinhardt | 52/22 |
| 3,393,055 | 7/1968 | Stevenson | 210/738 |
| 3,415,747 | 10/1968 | Glew | 210/729 |
| 3,534,116 | 10/1970 | Fuller | 210/634 |
| 3,594,313 | 7/1971 | Carlson | 210/709 |
| 3,663,685 | 5/1972 | Evans | 424/1 |
| 3,875,071 | 4/1975 | Grand | 252/106 |
| 3,892,800 | 7/1975 | Nickel et al. | 424/1 |
| 3,919,190 | 11/1975 | Barker et al. | 424/180 |
| 3,957,741 | 5/1976 | Rembaum et al. | 526/312 |
| 4,005,188 | 1/1977 | Tilly et al. | 424/5 |
| 4,009,232 | 2/1977 | Shiiki et al. | 264/9 |
| 4,059,624 | 11/1977 | Harrison | 260/404.5 |
| 4,105,598 | 8/1978 | Yen et al. | 521/53 |
| 4,180,619 | 12/1979 | Makhlouf et al. | 526/202 |
| 4,215,994 | 8/1980 | Kodras | 210/634 |
| 4,234,600 | 11/1980 | Sirrenberg et al. | 424/310 |
| 4,395,391 | 7/1983 | Pfeiffer et al. | 424/5 |
| 4,426,291 | 1/1984 | Sharangpani et al. | 210/634 |
| 4,515,695 | 5/1985 | Knorr, Jr. | 210/634 |

FOREIGN PATENT DOCUMENTS 867650 5/1961 United Kingdom.

OTHER PUBLICATIONS

Violante et al., "Biodistribution of a Particulate Hepatolienographic CT Contrast Agent," Inv. Radiol. 16:40 (1981).
Lauteala et al., "Effect of Intravenously Administered Iodipamide Ethyl Ester Particles on Rat Liver Morphology," Inv. Radiol. 19:133 (Mar.-Apr. 1984).
Violante et al., "Protein Binding to Iothalamate Ethyl Ester," Inv. Radiol., 14:177 (1979).
Violante et al., "Maximizing Hepatic Contrast Enhancement with a Particulate Contrast Agent in Computed Tomography,".
Vioilante and Fischer, "Particulate Suspensions as Contrast Media," ch. 13 in Handbook of Experimental Pharmacology, vol. 73 Sovak, ed. (Springer Berlin, 1984).
Grimes et al., "Formulation and Evolution of Ethiodized Oil Emulsion for Intravenous Hepatography," J. Pharmaceut. Sci 68: 52 (1979).

Primary Examiner—Peter Hruskoci
Attorney, Agent, or Firm—Kenyon & Kenyon

[57] ABSTRACT

The invention involves a method for making uniformly sized particles from water-insoluble drugs or other organic compounds. First, a suitable solid organic compound is dissolved in an organic solvent, and the solution can be diluted with a non-solvent. Then, an aqueous precipitating liquid is infused, precipitating non-aggregated particles with substantially uniform mean diameter. The particles are then separated from the organic solvent. Depending on the organic compound and the desired particle size, the parameters of temperature, ratio of non-solvent to organic solvent, infusion rate, stir rate, and volume can be varied according to the invention.

33 Claims, 6 Drawing Sheets

FIG. I.

METHOD FOR MAKING UNIFORMLY SIZED PARTICLES FROM WATER-INSOLUBLE ORGANIC COMPOUNDS

This application is a continuation-in-part of U.S. Ser. No. 612,725, filed May 21, 1984 now abandoned.

BACKGROUND OF THE INVENTION

Particles of compounds having low water-solubility are commonly used in a wide variety of applications, including ceramics, paints, inks, dyes, lubricants, pesticides, insecticides, fungicides, fertilizers, chromatography columns, cosmetics, lotions, ointments, and detergents. Aqueous dispersions of particles are used in many cases to avoid hazards such as flammability and toxicity associated with organic solvents. Such dispersions typically have a broad range of particle size.

In many cases product performance is improved by controlling the particle size distribution. In general, smaller particles of a compound will dissolve faster than larger particles of the same compounds. Control of particle size is, therefore, important in controlling the rate of solubilization.

Many drugs have been formulated as particles for controlled-release following oral administration or implantation. Particle size is one important factor affecting the release rate of these drugs. Those skilled in the art can discern other examples for using particle size to control product performance for the substances listed above.

Drugs that are insoluble in water can have significant benefits when formulated as a stable suspension of particles of less than three microns diameter. In this particulate form, the drug can be injected intravenously, circulate in blood, and be preferentially accumulated in, for example, the reticuloendothelial system, where it can facilitate normal reticuloendothelial functions such as detoxification. Alternatively, the drug can reside in the reticuloendothelial cells where it is stored until solubilized or metabolized into an active form which circulates in blood to other tissues for efficacy. This "slow" release of active drug can provide more constant drug concentrations in plasma over a period of hours, days, weeks, or months, resulting in improved therapeutic efficacy. Biodegradable particles which are radiopaque or labelled with a radioisotope are useful for diagnostic imaging of organs, such as liver and spleen, with high concentrations of fixed reticuloendothelial function.

Many advantages have already been recognized for insoluble particulate radiopaque contrast media, for example, as explained in "Improvement in Radiographic Contrast Media Through the Development of Colloidal or Particulate Media: an Analysis", by Harry W. Fischer, *Journal of Theoretical Biology;* 67: 653–670 (1977). More recent papers on this subject include Violante, M. R., Fischer, H. W., and Mohoney, J. A., "Particulate Contrast Media," *Invest. Radiol.,* 15: S329 November-December 1980; and Violante, M. R., Dean, P. B., Fischer, H. W., and Mahoney, J. A., "Particulate Contrast Media for Computer Tomographic Scanning of the Liver", Invest. Radiol., 15: 171 November-December 1980.

There are enormous medical implications for the intravenous administration of drugs formulated as suspensions of particles of three microns diameter, or less, which can be accumulated by phagocytic cells and slowly solubilized for sustained release into plasma for circulation to other organs and tissues. Obvious drug classes appropriate for formulation as particulate suspensions include: antineoplastics, antimicrobials, antivirals, anticoagulants, antihypertensives, antihistamines, antimalarials, male and female contraceptives, antiepileptics, depressants and antidepressants, adrenocortical steroids, hormones and hormone antagonists, cardiac glycosides, immunosuppressants, beta-blockers, water-insoluble vitamins, sympathomimetics, hypoglycemic agents, hyperglycemic agents, analgesics, tranquilizers, mood altering drugs, and others. The treatment of deficiency diseases, alcohol abuse, drug abuse, and many others could be improved with intravenous administration of particulate suspensions of the appropriate drug. Other medical applications for particulate drug suspensions will be apparent to those skilled in the art.

Accurate control of particle size is essential for safe and efficacious use of these formulations. Particles must be less than three microns in diameter to safely pass through capillaries without causing emboli. This is critical for intravenous administration since the particles must pass through lung capillaries before reaching the fixed reticuloendothelial cells of liver and spleen. Restriction to particle diameters of 0.01–0.1 micron could result in selective accumulation of these particles in certain tissues, eg., neoplastic tissue, where capillaries are somewhat more porous than capillaries of normal tissues. Suspensions of particles with diameters greater than 10 microns could be useful for selective intra-arterial administration to purposely embolize vessels feeding abnormal tissue such as a neoplasm. Accurate and precise control of particle diameters is essential for efficacy while minimizing or avoiding adverse effects in each of these applications.

Conventional methods of making water-insoluble compounds produce particles of many different sizes, many of which are unsuitable for the purpose at hand. Mechanically sorting or separating a desired particle size from a mix of sizes is difficult and unsatisfactory. Centrifuging and filtration do not produce high yields of particles that are all precisely the same desired size.

Investigations of water-insoluble radiopaque contrast materials required uniform particles in specific sizes that were very difficult to obtain by conventional methods. Precipitation as a way of directly forming particles of a predetermined size was then investigated. Partial success was achieved with one material and one method as reported in "Particulate Contrast Media", *Investigative Radiology,* 15: S329 November-December 1980; but this method would not work with other materials and would not allow accurate variation and control of the particle size produced.

Further investigation led to the invention of this application, which is effective with any drug or other compound having a solubility in water of preferably less than one part per ten thousand to obtain a predetermined particle size of the water-insoluble drugs or other compounds used in aqueous dispersions.

SUMMARY OF THE INVENTION

The invention involves a method of making uniformly sized particles of a solid, water-insoluble organic compound by, first, preparing a solution of the solid organic compound in a water-miscible organic solvent for the compound, the compound having essentially little aqueous solubility; second, infusing an aqueous precipitating liquid into the solution at a temperature between about −10° C. and about 100° C. and at an infusion rate of from about 0.01 ml per minute to about 1000 ml per minute per unit volume of 50 ml to produce a suspension of precipitated solid organic compound in the form of substantially non-aggregated particles with a substantially uniform mean particle diameter selected from the range of less than about 10 microns, such that the particle size is directly related to the solution temperature and inversely related to infusion rate, and then separating the particles from the organic liquids and washing in aqueous washing liquid. Agitation of the solution being infused with precipitating liquid is preferred. This can be accomplished by stirring, shaking, combining two streams of liquid, by the infusing itself and by other techniques known to those skilled in the art.

In preferred embodiments of the invention, additional aqueous precipitating liquid is added to the suspension before the particles are separated from the organic solvents. Separation can be accomplished, for example, by centrifugation, membrane filtration, reverse osmosis, or other methods.

The aqueous washing liquid can be the same as the aqueous precipitating liquid, and it can be pharmaceutically acceptable for injecting into a patient.

The aqueous precipitating liquid can be water, a solution of a mineral salt, or a surfactant solution. Suitable aqueous surfactant solutions include 5% polyvinyl pyrrolidone C-30, 0.1% polyvinyl pyrrolidone C-15, 0.1% human serum albumin, 0.1% Pluronic F-68 (poloxamer 188), and 0.33% gelatin, alone or combined with 0.6% hetastarch, 0.02% propylene glycol, or 2% sucrose. The aqueous precipitating liquid can be infused through a needle of standard gauge.

The mean particle diameter of the particles can be up to about 10 microns, preferably in a range of 0.01 microns to about 5 microns.

Particles made according to this invention will typically have a particle size distribution with a maximum relative standard deviation of 50%, for example 95% of the particle having a mean size of 1.0 micron will be within the size range of 0.5 to 1.5 microns.

The solid organic compound has, preferably, an aqueous solubility of less than about one part per ten thousand, and the compound may be organo-metallic. Generally, any compound that meets the other requirements of the invention is suitable, including many drugs. Where heparin complexes are used, no surfactant is necessary.

The organic solvent can be dimethyl sulfoxide, dimethyl formamide, N,N'-dimethyl acetamide, phenol, isopropanol, or other solvents.

In a preferred embodiment, the method includes the additional step of diluting the organic solution with a non-solvent liquid such that the ratio of non-solvent to solvent is between about 100:1 and about 1:100, after preparing the organic solution and before the infusion step, so that the particle size is directly related to the ratio of non-solvent to solvent.

In further preferred embodiments, the non-solvent is one in which the organic compound is slightly more soluble than in water. The non-solvent can be a lower aliphatic alcohol.

In particular preferred embodiments, iodipamide ethyl ester, an ethyl ester of a triiodobenzoic acid derivative, is dissolved in dimethyl sulfoxide and diluted with ethanol; if the ratio of ethanol to dimethyl sulfoxide is greater than about two, the mean particle diameter is greater than about one micron, and if the ratio of ethanol to dimethyl sulfoxide is less than about two, the mean particle diameter is less than about one micron.

DETAILED DESCRIPTION OF THE INVENTION

This invention concerns the preparation of water-insoluble compounds as uniform particles of a predetermined size. The particles are formed by a carefully controlled precipitation of the compound into an aqueous phase from an organic solvent in which the compound is soluble.

Figure 1:
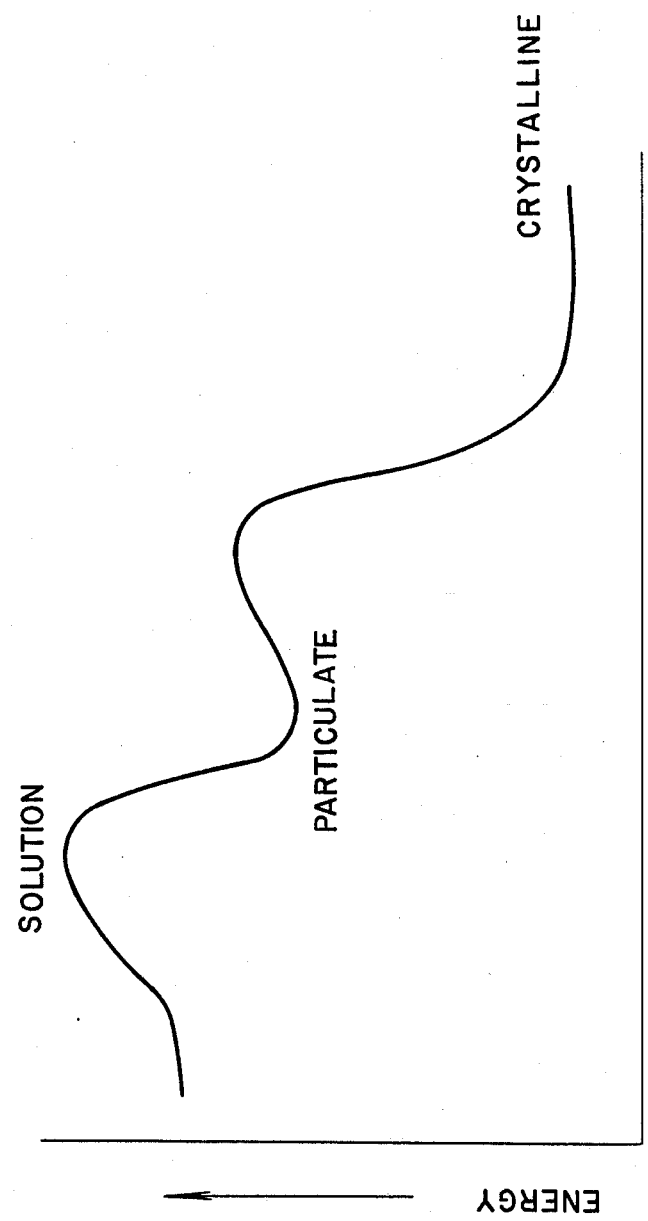
FIG. 1 is a graph of free energy of the various phases of the compounds used in the invention.
Figure 2:
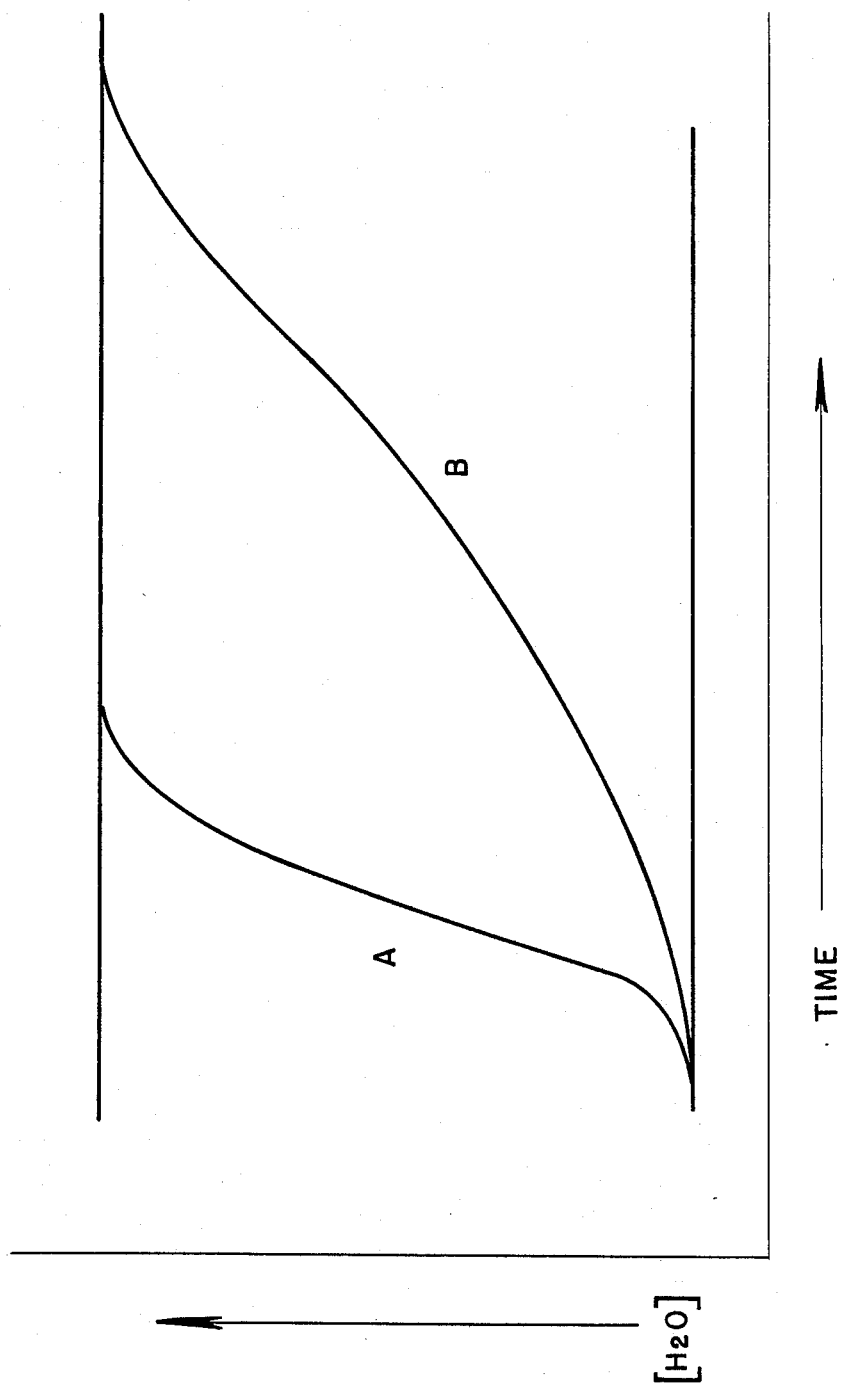
FIG. 2 is a graph of the relationship between size distribution of particles and time interval between onset and completion of precipitation.

The physical chemical principles thought to be involved in this invention are demonstrated in FIGS. 1 and 2. FIG. 1 shows that the free energy of the system is higher when the compound is dissolved in the organic solvent than when the compound exists in the particulate or crystalline state. During precipitation the compound will naturally convert to the crystalline form—the lowest free energy state—unless it is trapped in the metastable particulate form, a condition where its free energy is intermediate between the solution and the crystalline phases. When properly practiced, this invention enables the trapping of a compound in the metastable particle state, precluding transformation to the crystalline state.

The size distribution of particles formed during precipitation can be correlated with the time interval between onset and completion of precipitation. As shown in FIG. 2, a very short time interval results in the production of uniformly sized particles (A), while a very long time interval results in a broad particle size distribution (B). Intermediate conditions produce intermediate particle size distributions.

An important parameter for utilization of this invention is the aqueous solubility of the compound. The invention requires the use of solid organic compounds having essentially little aqueous solubility. We have found that compounds which have a water-solubility of less than one part in ten thousand are ideally suited for this technology. Compounds which are more water-soluble can be used with this invention; however, the higher the solubility the greater the probability that some of the compound will dissolve in the aqueous phase and transform to the more stable crystalline state. Also redissolution in the aqueous phase can lead to a broadening of the particle size distribution. For these reasons, we prefer compounds having a water-solubility of less than one part in ten thousand.

In order to make particles of a uniform and predetermined size having a solubility of less than one part per ten thousand, a solution of the solid organic compound in a suitable organic solvent is prepared. The solution may be diluted with a non-solvent that does not cause the drug or other compound to precipitate. An aqueous precipitating liquid is also prepared, preferably with a surfactant, in sufficient quantity to both precipitate the drug or other compound and stabilize the resulting suspension of particles of the compound against aggregation. Water may be used alone as the recipitating liquid when compounds which do not aggregate are used. The aqueous solution is infused into the organic solution under carefully controlled conditions, including: the rate of stirring of the organic solution, the rate of infusion of the aqueous solution, the volume of the organic solution and the temperature of the solutions and the suspension.

In investigations of varying parameters to adjust for particle size, three usable relationships were discovered: (1) diluting the solution with more of the non-solvent produces larger particles, and diluting with less of the non-solvent produces smaller particles; (2) higher temperatures of the solution during precipitation produce larger particles, and lower temperatures of the solution during precipitation produce smaller particles; and (3) at a given stirring rate of the organic solution, faster infusion rates of aqueous solution produce smaller particles while slower infusion rates produce larger particles.

When the precipitation is complete, the uniformly sized particles are separated from the liquid and washed to remove the organic solvent. In most cases, the particles should be separated from the liquid quickly to prevent transformation to a crystalline form.

Compounds that are used in the invention are solid organic materials, including organometallic compounds, that have a solubility in water of preferably less than one part per ten thousand. Otherwise the specific compound and its purpose are less important to the way the invention works.

The first step is to prepare a solution of the compound of interest in an organic solvent suitable for that compound. This can occur as the compound is synthesized as a dissolved solid, or it can be done by simply dissolving the compound in the solvent of choice.

The solvent is chosen to suit the compound. For example, dimethylformamide (DMF) is a solvent for iothalamate ethyl ester (IEE) and iosefamate ethyl ester (IFE), and dimethylsulfoxide (DMSO) is a solvent for iodipamide ethyl ester (IDE) and IEE. Any satisfactory solvent for the compound that is miscible with water can be used.

The next step is to dilute the solution with a non-solvent that does not cause the compound to precipitate. The non-solvent causes greater dispersion of the dissolved molecules of the compound in the liquid phase. Greater dilution of the solution with non-solvent produces larger particles, and less dilution of the solution with non-solvent produces smaller particles.

The non-solvent should not precipitate the compound when it is added to the solution. Non-solvents in which the compound is slightly more soluble than in water are preferred. Lower aliphatic alcohols, such as ethanol, are effective non-solvents for solutions of IDE and IEE in DMSO. For the ethyl esters of triiodobenzoic acid, proportions of non-solvent to solvent at a ratio of 2 or more can produce 1 to 3 micron sized particles (depending on other parameters); and ratios of less than 2 can produce sub-micron particles, at least as applied to DMSO solutions diluted with ethanol.

To precipitate the compound from the solution in a desired particle size, an aqueous solution of a surfactant is prepared in sufficient quantity to effect complete precipitation of the compound and to stabilize the resulting suspension of particles of the compound against aggregation. The surfactant provides the stabilization against aggregation, and the water is the precipitating agent. Presence of extra surfactant is advisable to ensure stabilization so that precipitated particles suspended in liquid do not aggregate, forming particles of an improperly large size. While surfactants are used in most cases, some compounds appear to form stable, substantially non-aggregated particles without the use of surfactants. Examples of such non-aggregrating compounds are certain Heparin complexes.

It is thought that particles with relatively high surface charge are less likely to require surfactant in the aqueous precipitating solution. The surface charge of a particle is sometimes referred to as its zeta potential, a measurement of charge which falls off with distance. There may be a threshold zeta potential above which no surfactant is needed, but below which, surfactant is needed to keep the precipitating particles from aggregating. The zeta potential is directly correlated with the polarity or net charge of an organic compound. Thus, the need for surfactant in the aqueous precipitating solution may be predicted from the extent of the charge or polarity of the organic compound employed in the method of the invention. For exmaple, heparin complexes are highly charged, and form stable non-aggregated particles when precipitated with water.

Generally, such a theory notwithstanding, empirical methods will suffice; that is, a precipitation may first be performed with water, and if aggregation occurs, then a precipitation in the presence of surfactant is indicated. Surfactants are chosen for their compatibility with the compound and their ability to stabilize a suspension of compound particles. For work with IEE and IDE drugs, a solution of 5% polyvinyl pyrrolidone (C-30), 0.1% polyvinyl pyrrolidone (C-15), or 0.1% human serum albumin is preferred. Also 0.1% Pluronic F-68, [Poloxamer 188, a poly(oxyethyleneco-oxypropylene) polymer], a 0.33% gelatin, 0.33% gelatin plus 0.6% Hetastarch, 0.33% gelatin plus 0.002% propylene glycol, and 0.33% gelatin plus 2% sucrose, or other surfactants known to one skilled in the art can be used.

To precipitate compound particles in the desired sizes, the aqueous solution and the organic solution are combined under controlled conditions of temperature, ratio of infusion rate to stirring rate, and the proportion of non-solvent to solvent in the dispersed solution.

The precipitation of the compound occurs exothermically, heating the organic solution and the resulting suspension. The temperature of the solution and resulting suspension is controlled to achieve the particle size of precipitate that is desired. Higher solution temperatures during precipitation produce larger particles, and lower solution temperatures during precipitation produce smaller particles.

Also, faster infusion rates at constant stirring rate of organic solution produce smaller particles, and slower infusion rates produce larger particles.

FIGS. three to five show the effects on particle size of varying parameters during precipitation of IDE from a DMSO solution diluted with 1 part solution to 2 parts ethanol using an aqueous solution of 5% polyvinyl pyrrolidone at different infusion rates and temperatures.

Figure 3:
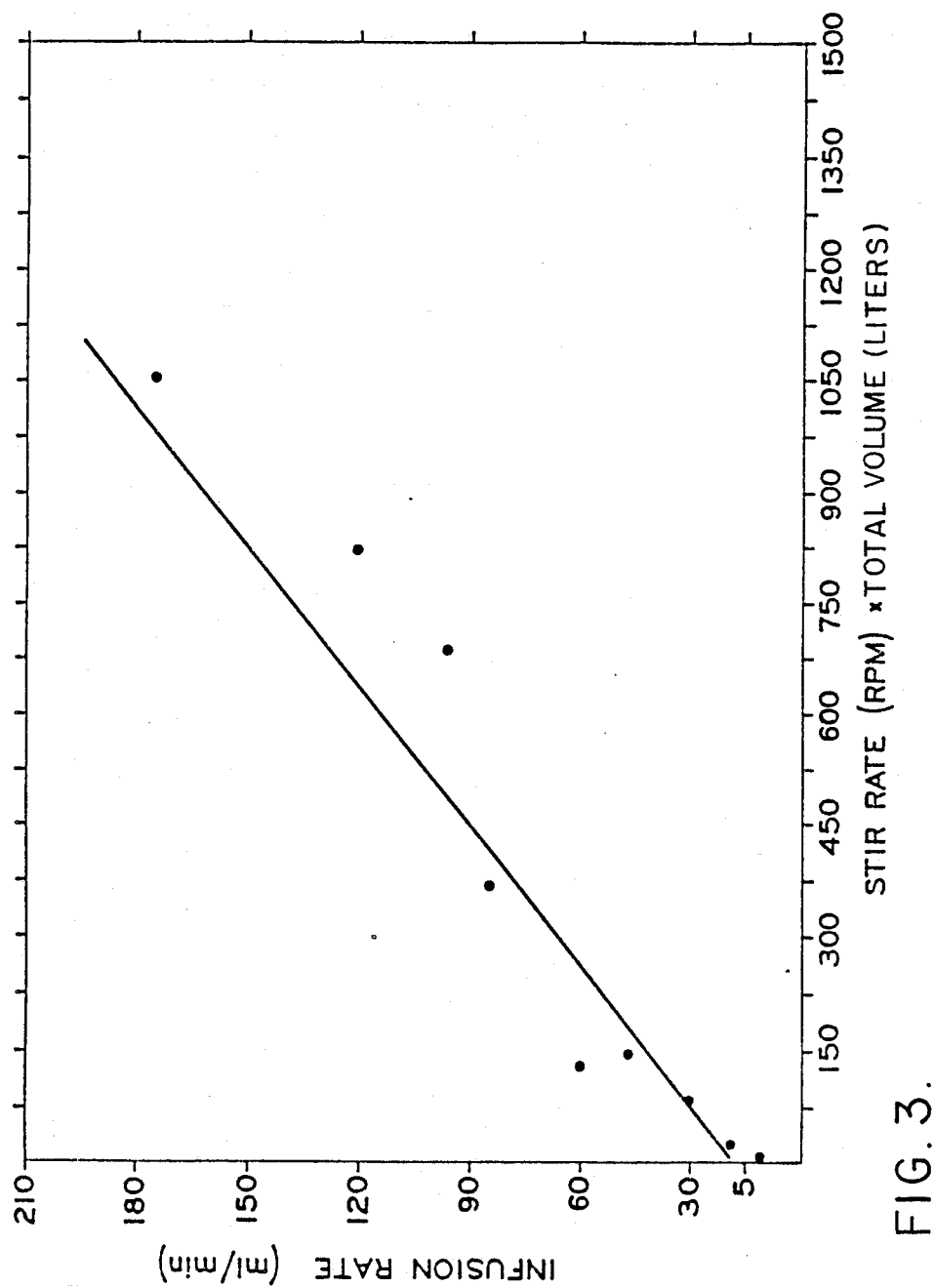
FIG. 3 is a graph of infusion rate (ml/min.) (of aqueous precipitating liquid) as a function of the product of stir rate (rpm) and total volume (liters) of the organic solution at a constant temperature; the relationship: aqueous infusion rate (ml/min.)=23+0.14 [stir rate (rpm)×volume organic solution (1)] defines the parameters for production of iodipamide ethyl ester particles of one micron diameter at a constant temperature (4° C.) and in dimethyl sulfoxide/ethanol.

FIG. 3 shows that as the volume and stirring rate of the organic compound iodipamide ethyl ester and dimethyl sulfoxide/ethanol solution are increased, the infusion rate of aqueous surfactant solution must be increased proportionally as defined by: infusion rate (ml/min.)=23+0.14 [volume (liters)×stir rate (r.p.m.)] to produce particles of 1 micron diameter at 4° C.

Figure 4:
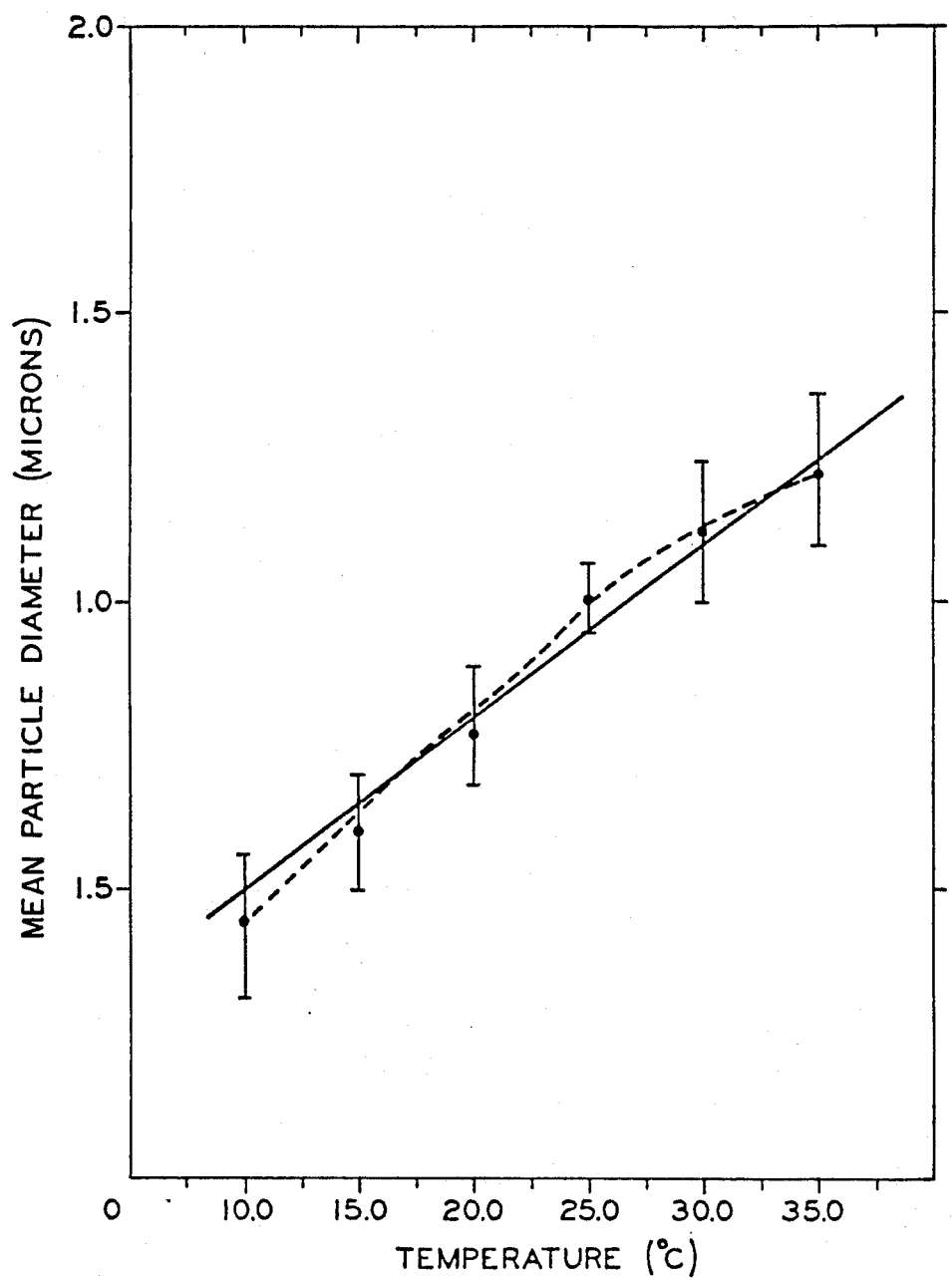
FIG. 4 is a graph showing iodipamide ethyl ester particle size as a function of temperature at a constant ratio of infusion rate of aqueous precipitating liquid to [stir rate (rpm)×volume of organic solution]

FIG. 4 shows that at a constant ratio of infusion rate to [stir rate×volume], increased precipitation temperature produces larger particles.

Figure 5:
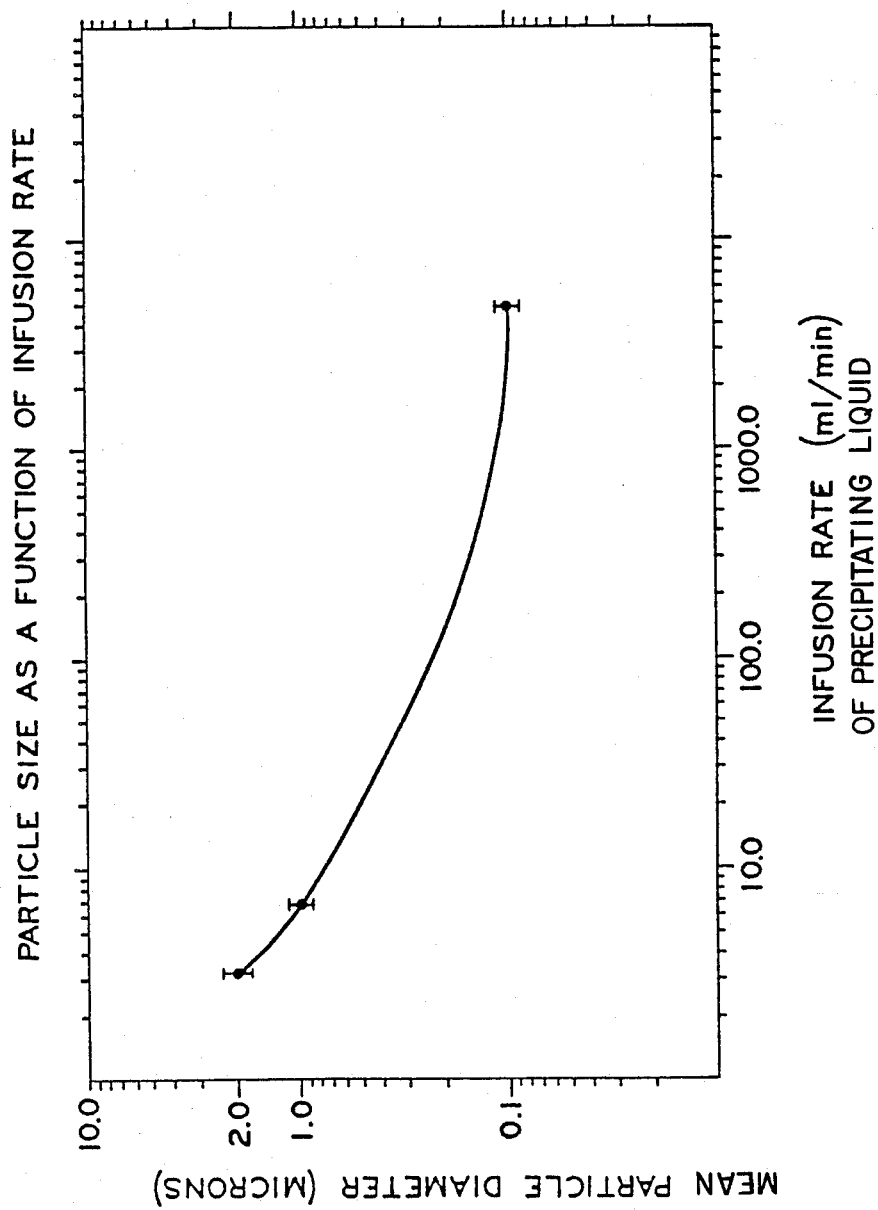
FIG. 5 is a graph demonstrating the effect on particle size of varying the infusion rate of aqueous precipitating liquid at constant temperature and stirring rate of an iodipamide ethyl ester solution.
Figure 6:
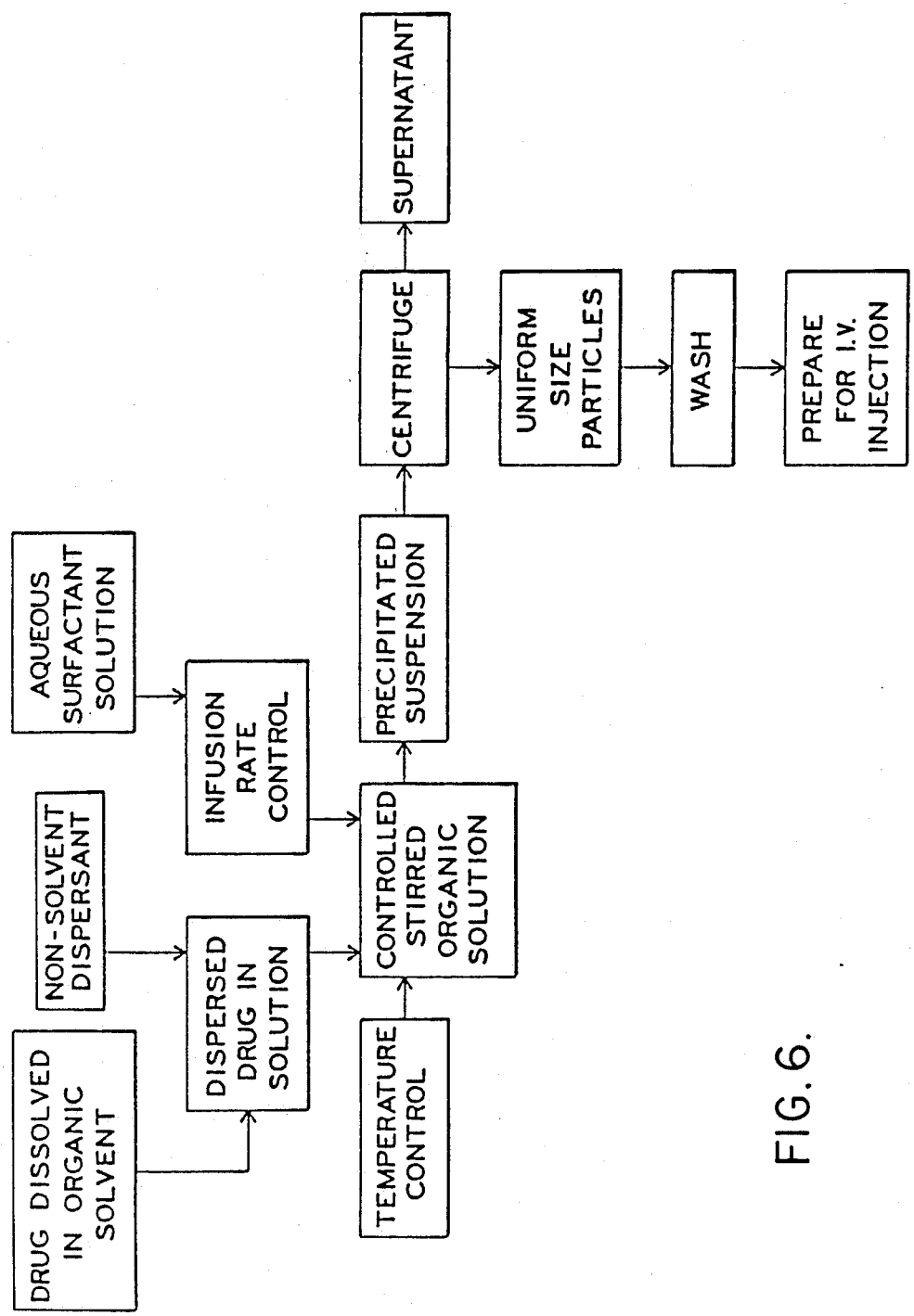
FIG. 6 is a schematic diagram of preferred steps in the inventive method.

FIG. 5 plots 3 points from the 20° C. temperature line of FIG. 3 for rate of infusion of the precipitation liquid into the organic solution to approximate the curve by which larger particles are formed from slower injection rates, showing that at a constant ratio of temperature to [stir rate×volume], particle size is inversely related to the rate of infusion of the precipitating liquid.

When FIGS. 3-5 are considered together, they show clearly that higher temperatures and slower mixing rates produce larger particles, and lower temperatures and faster mixing rates produce smaller particles. Another parameter that can be varied to affect particle size is the amount of dilution of the solution before precipitation occurs.

When the precipitation is complete, extra aqueous surfactant solution can be added to further stabilize the suspended particles against agglomeration. The extra solution can be added at a rapid rate, since essentially all the compound is now precipitated in uniformly sized particles. The precipitated particles are promptly separated from the organic solvents to prevent redissolving and reprecipitation of particles at undesirable sizes. Centrifuging is a preferred way to perform the separation. Other methods, including membrane filtration, reverse osmosis, and others known to persons skilled in the art may also be used to remove undesired substances. Promptly after separating the particles from the organic liquid, the particles are washed or rinsed with normal saline solution to remove solvent and excess surfactant.

The method of the invention is illustrated by the following examples which, however, do not limit the invention as described above and set forth in the claims.

Examples 1 to 19 are presented in Table I. The solid organic compound was dissolved in the organic solvent and then diluted (except where indicated) by the nonsolvent. The aqueous precipitating liquid was then infused through a needle at the given rate into the solution, at the given temperature and while stirring at the given stirring rate. The size of the particles obtained is shown for each example.

TABLE I

| | Example 1 | Example 2 | Example 3 | Example 4 | Example 5 | Example 6 | Example 7 |
|---|---|---|---|---|---|---|---|
| 1. solid organic compound | 10 mg 2,2',4,4'-tetrahydroxybenzophenone | 1.4 mg RS nitrocellulose compound (¼ sec) | 7 mg RS nitrocellulose (¼ sec.) | 10 mg progesterone | 5240 mg iosefamate ethyl ester | 10 g iothalamate ethyl ester | 100 mg beta-2,3,6 triod-3-dimethyl formamidino-phenyl propionic acid ethyl ester |
| 2. organic solvent | 0.2 ml dimethyl sulfoxide | 0.2 ml dimethyl sulfoxide | 0.4 ml dimethyl sulfoxide | 0.2 ml dimethyl sulfoxide | 60 ml dimethyl sulfoxide | 32 ml dimethyl sulfoxide | 2.0 ml dimethyl sulfoxide |
| 3. non-solvent | 0.2 ml ethanol (99%) | 0.2 ml ethanol (99%) | 0.01 ml isopropanol | 0.2 ml ethanol (99%) | 20 ml ethanol (99%) | — | 2.5 ml ethanol (99%) |
| 4. aqueous precipitating liquid | 5 ml human serum albumin (0.1%) | 5 ml human serum albumin (0.1%) | 5 ml human serum albumin (0.1%) | 5 ml human serum albumin (0.1%) | 400 ml polyvinyl pyrrolidone C-15 (5%) | 800 ml polyvinyl pyrrolidone C-15 (5%) | 25 ml Poloxamer 188 a poly (oxyethylene-co-oxypropylene) polymer (Pluronic F-68)(0.1%) |
| 5. infusion rate (ml./min.) of precipitating liquid | 2.5 | 2 | 2.5 | 2.5 (through an 18 gauge needle) | 3 | 300 | 750 |
| 6. stir rate (rev./min) | 200 | 400 | 200 | 200 | 200 | 300 | 650 |
| 7. temperature of solution | 20° C. | 20° C. | 20° C. | 20° C. | 20° C. | 0–2° C. initial 40° C. final | 10° C. |
| 8. particle diameter | 0.5 micron | 0.5 micron | 0.5 micron | 1 micron | 1.0 micron | 1.0 micron | 0.1 micron |

| | Example 8 | Example 9 | Example 10 | Example 11 | Example 12 | Example 13 | Example 14 |
|---|---|---|---|---|---|---|---|
| 1. solid organic compound | 100 mg beta-2,3,6 triod-3-dimethyl formamidino-phenyl propionic acid ethyl ester | 100 mg beta 2,4,6-triod-3-dimethyl formamidino phenyl propionic acid ethyl ester | 120 mg iodipamide ethyl ester | 1200 mg iodipamide ethyl ester | 120 mg iodipamide ethyl ester | 120 mg iodipamide ethyl ester | 10 mg isopropyl pyrrolizine derivative (NSC-278214) |
| 2. organic solvent | 2.0 ml dimethyl sulfoxide | 2.0 ml dimethyl sulfoxide | 2.0 ml dimethyl sulfoxide | 20 ml dimethyl sulfoxide | 2.0 ml dimethyl sulfoxide | 2.0 ml dimethyl sulfoxide | 0.4 ml dimethyl sulfoxide |
| 3. non-solvent | 2.5 ml ethanol (99%) | 2.5 ml ethanol (99%) | 2.5 ml ethanol (99%) | 25 ml ethanol (99%) | 2.5 ml ethanol (99%) | 2.5 ml ethanol (99%) | — |
| 4. aqueous precipitating liquid | 25 ml human serum albumin (0.1%) | 25 ml polyvinyl pyrrolidone C-15 (0.1%) | 5 ml polyvinyl pyrrolidone C-15 (0.1%) | 50 ml polyvinyl pyrrolidone C-15 (0.1%) | 5.0 ml polyvinyl pyrrolidone C-15 (0.1%) | 25 ml poly(oxyethylene co-oxypropylene) polymer, Poloxamer 188 (Pluronic F-65) (0.1%) | 5 ml human serum albumin (0.1%) |
| 5. infusion rate (ml./min.) of precipitating liquid | 750 | 750 | 300 | 19 | 2 | 750 | 20 |
| 6. stir rate (rev./min) | 650 | 650 | 80 | 190 | 200 | 700 | 300 |
| 7. temperature of solution | 10° C. | 10° C. | 4° C. | 10° C. | 10° C. | 0° C. | 17° C. |
| 8. particle diameter | 0.1 micron | 0.1 micron | 0.1 micron | 1.5 micron | 1.0 micron | 0.1 micron | 0.5 micron |

| Example 15 | Example 16 | Example 17 | Example 18 | Example 19 | Example 20 |
|---|---|---|---|---|---|

TABLE I-continued

| | | | | | |
|---|---|---|---|---|---|
| 1. solid organic compound | 10 mg isopropyl pyrrolizine derivative (NSC-278214) | 10 mg isopropyl pyrrolizine derivative (NSC-278214) | 1.5 mg. 1,2 diamino-cyclohexane malinate platinum (II) | 10 mg N—(trifluoroacetyl) adriomycin 14 valerate | 200 mg heparin-benzal-konium chloride complex | 10 mg organic compound* (see list) |
| 2. organic solvent | 0.4 ml N,N'—dimethyl acetamide | 0.4 ml dimethyl sulfoxide 0.2 ml ethanol (99%) | 0.05 ml phenol | 0.2 ml dimethyl sulfoxide 0.2 ml ethanol (99%) | 10 ml isopropanol | 0.2 ml dimethyl sulfoxide 0.2 ml ethanol (99%) |
| 3. non-solvent | — | — | 0.45 ml m-amino-phenol and 0.25 ml ethanol (99%) | | — | |
| 4. aqueous precipitating liquid | 20 ml human serum albumin (0.1%) | 20 ml human serum albumin (0.1%) | 5 ml human serum albumin (0.1%) | 5 ml human serum albumin (0.1%) | 200 ml water | 5 ml human serum albumin (0.1%) |
| 5. infusion rate (ml/min.) of precipitating liquid | 38 | 100 | 5 | 2.5 | 3.7 | 2.5 |
| 6. stir rate (rev./min) | 50 | 200 | 200 | 200 | 300 | 250 |
| 7. temperature of solution | 0° C. | 0° C. | 20° C. | 20° C. | 20° C. | 20° C. |
| 8. particle diameter | 0.5 micron | 0.1 micron | 0.1 micron | 1.0 micron | 0.5 micron | 1.0 micron |

*norethisterone, acetyl salicylic acid, wafarin, heparin-tridodecyl methyl ammonium chloride complex, sulfamethoxazole, cephalexin, prednisolone acetate, diazepam, clonazepam, methidone, naloxone, disulfiram, mercaptopurine, digitoxin, primaquine, mefloquine, atropine, scopolamine, thiazide, furosemide, propanelol, methyl methacrylate, poly methyl methacrylate, 5-fluorodeoxyuridine, cytosine arabinoside, acyclovir, levonorgestrel Examples 1 to 19 show how the process can be used to produce aqueous dispersions of a wide variety of compounds that have low aqueous solubility and for which particle size can be controlled with substantial precision and predictability. Conditions would be varied from compound to compound according to the invention in order to optimize results. This may in some cases include chemical modification of the compound to achieve the desired solubility.

Because of the range of examples presented above, it is reasonable to one skilled in the art, that numerous other compounds would be expected to behave in similar fashion.

Example 20 is also presented in Table I. This example should be performed in the same manner as examples 1 to 19, and would make particles of the listed compounds within the scope of the invention.

Examples 21 to 28 are presented in Table II. In each example, the given quantity of iodipamide ethyl ester was dissolved in the given volume of dimethyl sulfoxide, then diluted with the given volume of ethanol. The aqueous precipitating liquid was prepared from polyvinylpyrrolidone then infused at the given infusion rate through a needle with the given gauge into the solution while the solution was stirred at the given stir rate. The precipitation was carried out in the given vessel at the given temperature. After precipitation, the given amount of saline was added to further stabilize the dispersion. In each example, the mean particle diameter was about 1.0 micron and substantially uniform.

microns in diameter. In light of the problems that rough contours could damage vascular endothelial cells and promote aggregation, and that large particles could create pulmonary emboli, the method of this invention provides a more refined procedure for controlling particle size and shape.

Particle Precipitation Procedure.

Physical methods for modifying and controlling particle size, such as ball milling, grinding or sonication result in preparation with a very broad range of particle diameters. These methods are commonly used to eliminate large particles (greater than 4–5 microns), which could embolize in the pulmonary capillary bed, but generally some particles of submicron size are also produced; these very small particles have been shown to be more toxic than 1–2 micron particles, possibly due to increased protein binding resulting from the much larger surface area inherent with particles of smaller diameters, or possibly because of excessive uptake by bone marrow cells.

A chemical precipitation procedure for producing particles of a given size was developed to avoid these problems. By adding an aqueous solution of polyvinyl pyrrolidone, at controlled rates and temperatures, to IDE dissolved in a dimethyl sulfoxide/ethanol solvent, apparently spherical, amorphous particles can be produced with an extremely narrow size distribution. For a particle preparation with a mean diameter of 1 micron, the total range of particle diameters is 0.4 to 2.0 microns

TABLE II

| Parameters for Iodipamide Ethyl Ester Particle Precipitation | | | | | | | | |
|---|---|---|---|---|---|---|---|---|
| | Example 21 | Example 22 | Example 23 | Example 24 | Example 25 | Example 26 | Example 27 | Example 28 |
| Material iodipamide ethyl ester (60 mg/ml) | 0.5 gm 10 ml | 1 gm 20 ml | 2 gm 40 ml | 3.5 gm 70 ml | 5 gm 100 ml | 10 gm 200 ml | 20 gm 400 ml | 40 gm 800 ml |
| ethanol (99%) | 12.5 ml | 25 ml | 50 ml | 87.5 ml | 125 ml | 250 ml | 500 ml | 1,000 ml |
| polyvinyl pyrrolidone | 25 ml | 50 ml | 100 ml | 175 ml | 250 ml | 500 ml | 1,000 ml | 2,000 ml |
| 0.9% saline | 15 ml | 30 ml | 60 ml | 105 ml | 150 ml | 300 ml | 600 ml | 1,200 ml |
| stir rate | 125 rpm | 190 rpm | 300 rpm | 330 rpm | 200 rpm | 300 rpm | 175 rpm | 210 rpm |
| temperature | 4° C. | 4° C. | 4° C. | — | — | — | — | — |
| infusion rate | 11 ml/min | 19 ml/min | 30 ml/min | 45 ml/min | 60 ml/min | 85 ml/min | 120 ml/min | 175 ml/min |
| infusion needle size | 19 g | 19 g | 19 g | 19 g | 18 g | 18 g | 16 g | 16 g |
| S.B. length | 1.5" | 1.5" | 1.5" | 1.88" | 2.75" | 2.75" | 3.25" | 3.25" |
| vessel diam. | 2.38" | 2.38" | 2.38" | 3.38" | 5.0" | 5.0" | 8.6" | 8.6" |
| vessel | 250 ml polypropylene bottle | 250 ml polypropylene bottle | 250 ml polypropylene breaker | 1,000 ml glass beaker | 2,000 ml glass beaker | 2,000 ml glass | 9 L Bellco vessel | 9 L Bellco vessel |

EXAMPLE 29

PREPARATION OF IODIPAMIDE ETHYL ESTER PARTICLES FOR ADMINISTRATION TO A PATIENT

Particles of iodipamide ethyl ester (IDE) with a size of about 1 micron may be prepared for administration to a patient. IDE is the water-insoluble ethyl ester of iodipamide, a water-soluble radiopaque compound used clinically for radiographic examination of the gallbladder. The synthesis of iodipamide ethyl ester is known in the art (for exmaple, esterification by alcohol and acid or by a Schotten-Bauman reaction).

IDE is only minimally soluble in water ($10^{-5}$M) and can be precipitated easily from the dimethyl sulfoxide (DMSO)/ethanol solvent mixture. However, the simple addition of water to this solution results in IDE particles with extremely rough contours; these particles vary in size from less than one micron to greater than 300 with 90 percent of the particles ranging in size between 0.5 and 1.5 microns, as determined by microscopy.

By carefully controlling precipitation parameters, particle preparations demonstrating different mean diameters, but with a similarly small range of diameters, can be produced.

The IDE particles produced using this methodology are stable in whole blood with little apparent tendency toward aggregation. When suspended in whole blood, there is essentially no tendency for one micron IDE particles to aggregate with themselves or with formed elements of blood. The IDE particles have smooth contours.

We claim:

1. A method of making uniformly sized particles of a solid, water-insoluble organic compound, comprising:
   (a) preparing a solution of the solid organic compound in a water-miscible organic solvent for the compound, the solid organic compound having essentially little aqueous solubility;

(b) infusing an aqueous precipitating liquid into the organic solution at a temperature between about −10° C. and about 100° C. and at an infusion rate of from about 0.01 ml per min. to about 1000 ml per min. per 50 ml unit volume of solution, so as to produce a suspension of precipitated amorphous, non-crystalline solid organic compound in the form of substantially non-aggregated particles of a uniform size selected from a particle diameter range of up to about 10 microns, the particle size being directly related to the solution temperature during precipitation and inversely related to the infusion rate;

(c) separating the particles from the organic liquids and washing in aqueous washing liquid.

2. The method according to claim 1, wherein additional aqueous precipitating liquid is added to the suspension before the particles are separated.

3. The method according to claim 1, wherein the particles are separated by centrifugation, membrane filtration, or reverse osmosis.

4. The method according to claim 1, wherein the aqueous washing liquid is the same as the aqueous precipitating liquid.

5. The method according to claim 1, wherein the aqueous washing liquid is pharmaceutically acceptable for injection into a patient.

6. The method according to claim 1, wherein the aqueous precipitating liquid is selected from the group consisting of water and an aqueous solution of a mineral salt.

7. The method according to claim 1, wherein the aqueous precipitating liquid is a surfactant solution.

8. The method according to claim 1, wherein the precipitating liquid is a surfactant solution selected from the group consisting of 5% polyvinyl pyrrolidone in water, 0.1% polyvinyl pyrrolidone in water, 0.1% human serum albumin in water, 0.1% in water of a poly (oxyethylene -co-oxypropylene) polymer, 0.33% gelatin in water, 0.33% gelatin and 0.6% hetastarch in water, 0.33% gelatin and 0.02% propylene glycol in water, and 0.33% gelatin and 2% sucrose in water.

9. The method according to claim 1, wherein the step of infusing aqueous precipitating liquid is carried out by means of a needle of standard gauge.

10. The method according to claim 1, wherein the mean particle diameter is selected from the range of from about 0.01 micron to about 0.1 micron.

11. The method according to claim 1, wherein the mean particle diameter is selected from the range of from about 1 micron to about 4 microns.

12. The method according to claim 1, wherein the mean particle diameter is from about 1 to about 10 microns.

13. The method according to claim 1, wherein the solid organic compound has an aqueous solubility of less than about one part per ten thousand at ambient temperature.

14. The method according to claim 1, wherein the solid organic compound is an organometallic compound.

15. The method according to claim 1, wherein the solid organic compound is selected from the group consisting of an antineoplastic, an antimicrobial, an antiviral, an anticoagulant, an antihypertensive, an antihistamine, an antimalarial, a contraceptive, an antiepileptic, a depressant, an antidepressant, an adrenocortical steroid, a hormone, a hormone antagonist, a cardiac glycoside, an immunosuppressant, a beta-blocker, a water-insoluble vitamin, a sympathomimetic, a hypoglycemic agent, a hyperglycemic agent, an analgesic, a tranquilizer, and a mood-altering drug.

16. The method according to claim 1, wherein the solid organic compound is an ethyl ester of a triiodobenzoic acid derivative.

17. The method according to claim 1, wherein the solid organic compound is selected from the group consisting of iodipamide ethyl ester, iothalamate ethyl ester, iosefamate ethyl ester, 2,2',4,4'-tetrahydroxybenzophenone, RS nitrocellulose, progesterone, beta-2,4,6-triiodo-3-dimethyl formamidinophenyl propionic acid ethyl ester, isopropylpyrrolizine derivative (NSC-278214), N-(trifluoroacetyl) Adriamycin 14 valerate, and 1,2 diaminocyclohexane malinate platinum (II).

18. The method according to claim 1, wherein the solid organic compound is selected from the group consisting of norethisterone, acetyl salicylic acid, wafarin, heparintridodecyl methyl ammonium chloride complex, sulfamethoxazole, cephalexin, prednisolone acetate, diazepam, clonazepam, methidone, naloxone, disulfiram, mercaptopurine, digitoxin, primaguine, mefloquine, atropine, scopolamine, thiazide, furosemide, propanelol, methyl methacrylate, poly methyl methacrylate, 5-fluorodeoxyuridine, cytosine arabinoside, acyclovir, levonorgestrel.

19. The method according to claim 1, wherein the organic solvent is from the group consisting of dimethyl sulfoxide, dimethyl formamide, N,N'-dimethyl acetamide, phenol, and isopropanol.

20. The method according to claim 1, wherein the solid organic compound is a heparin complex, the organic solvent is isopropanol, and the aqueous precipitating liquid is water or an aqueous mineral salt solution.

21. The method according to claim 1, which further comprises the step of diluting the organic solution with a non-solvent liquid such that the ratio of non-solvent to solvent is between about 100:1 and about 1:100, after the preparation of the solution and before the infusion step, the particle size being directly related to the ratio of non-solvent to solvent.

22. The method according to claim 21, wherein the non-solvent liquid is one in which the solid organic compound is slightly more soluble than in water.

23. The method according to claim 21, wherein the non-solvent liquid is a lower aliphatic alcohol.

24. The method according to claim 21, wherein the solid organic compound is selected from the group consisting of iodipamide ethyl ester and iosefamate ethyl ester, the organic solvent is dimethyl sulfoxide, the non-solvent liquid is ethanol, the ratio of ethanol to organic solution is greater than about 2.0, and the mean particle diameter is greater than 1 micron in diameter.

25. The method according to claim 21, wherein the solid organic compound is selected from the group consisting of iodipamide ethyl ester and iosefamate ethyl ester, the organic solvent is dimethyl sulfoxide, the non-solvent liquid is ethanol, the ratio of ethanol to organic solution is less than about 2.0, and the mean particle diameter is less than about one micron in diameter.

26. The method according to claim 21, wherein the solid organic compound is iodipamide ethyl ester, the organic solvent is dimethyl sulfoxide, the non-solvent is ethanol, the aqueous precipitating liquid is 5% polyvinyl pyrolidone in water, the temperature is 4° C., and the infusion rate (ml/min) equals 23+0.14 [stir rate (r.p.m.)]×[volume organic solvent (liters)], and the mean particle diameter is about 1 micron diameter.

27. The method according to claim 1 wherein the mean particle diameter is selected from the range of from about 0.01 micron to about 10 microns.

28. The method according to claim 1 wherein the mean particle diameter is selected from the range of from about 0.01 micron to about 5 microns.

29. The method according to claim 1 wherein the particle size distribution has a maximum relative standard deviation of 50 percent.

30. The method according to claim 1 wherein the organic solution is agitated while the precipitating liquid is being infused.

31. The method according to claim 1 wherein the step of infusing the aqueous precipitating liquid is carried out by combining a stream of the organic solution with a stream of the aqueous precipitating liquid.

32. The method according to claim 31, wherein the separating step is carried out by continuous centrifugation or filtration.

33. The method according to claim 1, further comprising, before step (b), the step of measuring the zeta potential of the solid organic compound and using the zeta potential to select a surfactant and to determine the amount of surfactant in the aqueous precipitating liquid which is required to prevent aggregation of particles.

* * * * *